United States Patent
Porter et al.

(10) Patent No.: US 6,736,978 B1
(45) Date of Patent: May 18, 2004

(54) METHOD AND APPARATUS FOR MAGNETORESISTIVE MONITORING OF ANALYTES IN FLOW STREAMS

(75) Inventors: Marc D. Porter, Ames, IA (US); Jing Ni, San Jose, CA (US); G. Brent Dawson, San Jose, CA (US); Ruth Shinar, Ames, IA (US); Robert J. Lipert, Ames, IA (US); Michael C. Granger, Gilbert, IA (US); Mark Tondra, Minneapolis, MN (US)

(73) Assignee: Iowa State University Research Foundation, Inc., Ames, IA (US)

( * ) Notice: Subject to any disclaimer, the term of this patent is extended or adjusted under 35 U.S.C. 154(b) by 160 days.

(21) Appl. No.: 10/017,467

(22) Filed: Dec. 13, 2001

Related U.S. Application Data
(60) Provisional application No. 60/255,211, filed on Dec. 13, 2000.

(51) Int. Cl.[7] ............................................. G01N 33/553
(52) U.S. Cl. ................. 210/695; 210/746; 210/222; 210/243; 436/526; 436/806; 436/149; 436/150; 341/252
(58) Field of Search ................ 210/695, 746, 210/222, 243; 436/526, 806, 149, 150; 341/252

(56) References Cited

U.S. PATENT DOCUMENTS

| | | |
|---|---|---|
| 5,656,429 A | 8/1997 | Adelman |
| 5,932,813 A | 8/1999 | Swartzel et al. |
| 5,981,297 A | 11/1999 | Baselt |
| 5,985,153 A | 11/1999 | Dolan et al. |
| 6,013,188 A | 1/2000 | Terstappen et al. |
| 6,046,585 A | 4/2000 | Simmonds |
| 6,057,167 A | 5/2000 | Shieh et al. |

FOREIGN PATENT DOCUMENTS

WO    WO01/14591 A1    3/2001

OTHER PUBLICATIONS

Julia Boguslavsky, Lab–on–a–Chip: Easier, Faster, Smaller, Drug Discovery & Development, Jul./Aug. 2001.
R.L. Edelstein, et al., The BARC biosensor applied to the detection of biological warfare agents, 2000 Elsevier Science S.A.
David R. Baselt, et al., A biosensor based on magnetoresistance technology, 1998 Elsevier Science S.A.
Christine Berggren Driz, et al., Magnetic Permeability Measurements in Bioanalysis and Biosensors, Analytical Chemistry, vol. 68, No. 11, Jun. 1, 1996.
Emmanuel Delamarche, et al., Microfluidic Networks for Chemical Patterning of Substrates: Design and Application to Bioassays, 1998 American Chemical Society.
C. Bor Fuh, Split–flow Thin Fractionation, Analytical Chemistry, Apr. 1, 2000.

*Primary Examiner*—David A. Reifsnyder
(74) *Attorney, Agent, or Firm*—Leydig, Voit & Meyer, Ltd.

(57) ABSTRACT

Method and apparatus for manipulating and monitoring analyte flowing in fluid streams. A giant magnetoresistive sensor has an array of sensing elements that produce electrical output signals which vary in dependence on changes in the magnetic field proximate the sensing elements. The analyte is included in a stream, such that the stream has a magnetic property which is dependent on the concentration and distribution on the analyte therein. The stream is flowed past the giant magnetoresistive sensor and in sufficiently close proximity to cause the magnetic properties of the stream to produce electrical output signals. The electrical output signals are monitored as an indicator of analyte concentration or distribution in the stream flowing past the GMR sensor. Changes in the magnetic field produced by the background stream are introduced by analyte molecules, whose presence in the flow past the GMR will effect the output reading.

8 Claims, 8 Drawing Sheets

METHOD AND APPARATUS FOR MAGNETORESISTIVE MONITORING OF ANALYTES IN FLOW STREAMS

CROSS-REFERENCE TO RELATED PATENT APPLICATIONS

This patent application claims the benefit of U.S. provisional application No. 60/255,211, filed Dec. 13, 2000.

STATEMENT REGARDING FEDERALLY SPONSORED RESEARCH OR DEVELOPMENT

This invention was developed with governmental assistance under NSF Contract No. BES-0088241. The government may have certain rights in this invention.

FIELD OF THE INVENTION

This invention relates to microfluidics, to on-chip manipulation of analytes in fluid streams, and to monitoring for the presence and concentration of analytes in fluid (i.e., liquid or gas) streams.

BACKGROUND OF THE INVENTION

For low levels of detection, bioassays usually require labels or tags which connect the recognition process to a transduction mechanism. Such labels include radioactive compounds, enzymes and light emitting materials. Radioactive labels are useful in that they offer a low level of detection, but they require expensive detectors, present a potential radiohazard, and can be unstable. In comparison, enzymatic labels are more stable, less hazardous, and less expensive, but are not as sensitive. Light emitting labels, though sensitive, require specialized detectors and labels, which are bulky and/or expensive.

In recent years there has been an increasing interest in magnetic labels for chemical and bioanalysis, as exemplified by the interest in immunomagnetic separation technology, which is a proven method for such tasks as monitoring parasites in raw surface water. In that particular example, the requirements of parasite filtration, concentration, separation, and monitoring require bulky instrumentation and manual operation. One such example is described in Kriz; C. B.; Radevik, K; Kriz, D. *"Magnetic Permeability Measurements in Bioanalysis and Biosensors,"* Anal. Chem. 1996, 68, 1966, in which a ferromagnetic sample is placed in a container which in turn is placed in a measuring inductor electrically connected in a bridge sensing circuit.

There have been investigations that have demonstrated the feasibility of magnetic detection concepts as applied to biomolecules. Insofar as applicants are aware, that work has been limited to attempts to utilize the high sensitivity of giant magnetoresistive sensors (GMRs) for antibody and DNA detection through immobilization of capture molecules on GMR surfaces. These investigations recognize the high sensitivity of giant magnetoresistive sensors for antibody and DNA detection, but require the mechanism of immobilization of capture molecules on GMR surfaces. The capture molecules bind the magnetically labeled target analyte resulting in a change in the GMR resistance. This approach, which requires recognition specificity of binding between the capture and target molecules, can suffer from non-specific interactions that will affect the GMR reading and consequently compromise the level of detection. It also requires the selective binding of the analyte directly onto the surface of the GMR. U.S. Pat. No. 5,981,297 discloses the binding to a giant magnetoresistive sensor of binding molecules which are capable of immobilizing the target molecules. The output of the devices is then a measure of the number of analyte or target molecules bound to the cells of the sensor. In this arrangement, the goal is for rapid detection stated to be on the order of 15–30 minutes per assay.

SUMMARY OF THE INVENTION

In view of the foregoing, it is the general aim of the present invention to utilize magnetic detection for monitoring analytes flowing in liquid and air streams.

In that regard it is an object to utilize the high sensitivity of the giant magnetoresistive sensor, and to position such a sensor in close proximity to a flowing stream containing the analyte.

It is a further object to utilize detection of such a sensor based on either the intrinsic magnetism of the analyte or on the magnetism of a label bound to the analyte.

In accordance with the invention there is provided a method of monitoring analyte flowing in fluid streams. A giant magnetoresistive sensor has a plurality of sensing elements that produce electrical output signals; the signals vary dependent on changes in the magnetic field proximate the elements. A stream including the analyte is provided, the stream having a magnetic property that is dependent on the concentration and distribution of analyte therein. The magnetic property can be imparted by use of ferromagnetic particles or by use of paramagnetic or superparamagnetic particles in conjunction with application of a magnetic field. The stream is flowed past the giant magnetoresistive sensor in sufficiently close proximity to cause the magnetic properties of the stream to produce electrical output signals from the GMR. Electrical signals are monitored as an indicator of the analyte concentration or distribution in the stream flowing past the GMR.

Apparatus for practicing the method includes a giant magnetoresistive sensor having a plurality of sensing elements for detecting localized changes in the magnetic field proximate the elements. Microfluidic channels are associated with the GMR sensor closely proximate the elements of the sensor. The proximity is such that the paramagnetic particles flowing in the channels will cause an output from the GMR sensor that is indicative of the concentration or distribution of magnetic particles. A source of analyte in a fluid stream is altered such that the fluid stream has a magnetic property that is related to the concentration or distribution of the analyte in the stream. The fluid source is connected to the microfluidic channels for flowing a stream including the analyte past the GMR sensor. An electrical monitor is responsive to the GMR sensor for measuring and recording changes in the output signal as an indication of the magnetic properties and therefore analyte concentration or distribution in the stream flowing past the GMR sensor.

Other objectives and advantages of the invention will become more apparent from the following detailed description when taken in conjunction with the accompanying drawings.

BRIEF DESCRIPTION OF THE DRAWINGS

The accompanying drawings incorporated in and forming a part of the specification illustrate several aspects of the present invention, and together with the description serve to explain the principles of the invention. In the drawings.

While the invention will be described in connection with certain preferred embodiments, there is no intent to limit it to those embodiments. On the contrary, the intent is to cover all alternatives, modifications and equivalents as included within the spirit and scope of the invention as defined by the appended claims.

DETAILED DESCRIPTION OF THE INVENTION

Figure 1:
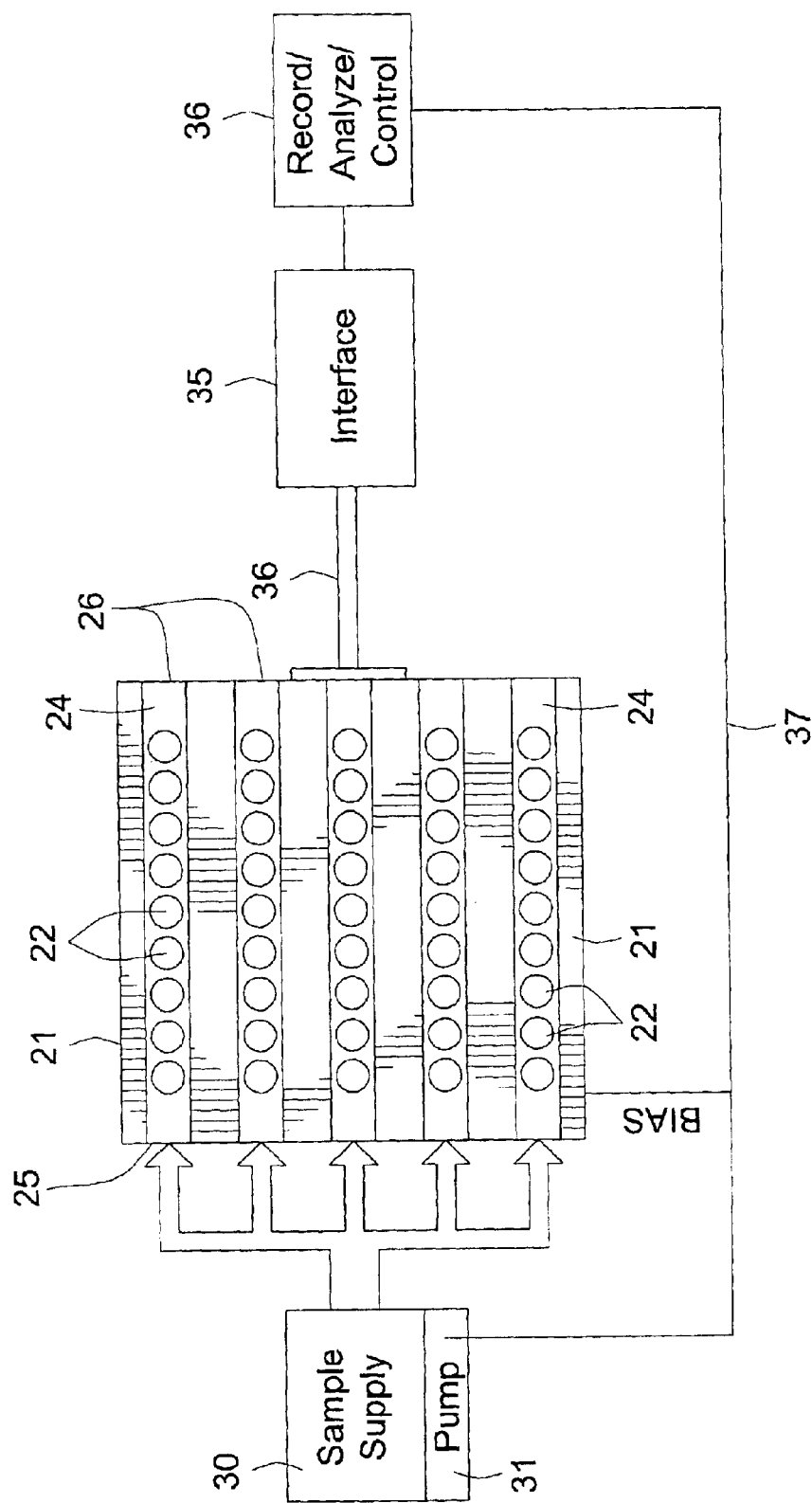
FIG. 1 is a block diagram illustrating a system constructed in accordance with the present invention.

Turning now to the drawings, FIG. 1 shows the general scheme of a detection system and method in accordance with the present invention. The detector assembly itself is a giant magnetoresistive sensor 21 GMR, and comprises an integrated circuit having a plurality of sensor elements formed in an array across its planar surface. Individual sensor elements are shown at 22, for example.

In contrast to prior sensors that utilize techniques to cause the analyte to bind at the sensor cell locations 22, the sensor 21 of the present invention includes structure for causing the analyte fluid to flow across the face of the sensor in proximity to the cells 22. In the illustrated embodiment, that flow structure is illustrated by a plurality of microfluidic channels 24, having an inlet side 25 and a outlet side 26. Although not illustrated, a sample collection container would typically by included after the outlet side 26. The microfluidic channels 24 provide microminiature conduits for flow of analyte across the surface of the cells 22 on the GMR 21. Flow channels molded in poly (dimethyl siloxane) (PDMS), as described in the literature can be utilized for the micro channels. (For example, see Delamarche, E.; Bernard, A.; Schmid, H.; Bietsch, A.; Michel, B.; Biebuych, H. "Microfluidic Networks for Chemical Patterning of Substrates: Designs and Application to Bioassays" J. Am. Chem. Soc. 1998, 120, 500). Associated with the micro channels is a sample supply 30, usually fitted with a pump, such as an off-chip syringe pump that causes fluid flow to and through the channels. Microfluidic channel structures including magnetic sorters and magnetic pumps that can be used to feed the channels on the GMR sensor are disclosed in detail in a subsequent portion of this specification.

An electrical interface 35 is electrically connected to the GMR 21, such as by bus 36 that connects the interface 35 to the cells 22 in the GMR 21. Connection can be to groups of sensing elements in series or parallel, or to individual elements, as is most appropriate to the application. The signals received from the GMR (which will be described in greater detail below) are sensed in the interface 35 and are passed to an electronic module 36 that is utilized to record and analyze the signals temporally with the flow across the sensor. The interface 35 can typically be in the form of electronic circuitry formed directly on the chip that carries the GMR. The record/analyze module 36 is often a personal computer connected to the analyzing system. The module 36 also has control aspects that are represented by an output line 37 connected to the GMR for bias purposes and to the pump 31 in the supply for control purposes.

Figure 3:
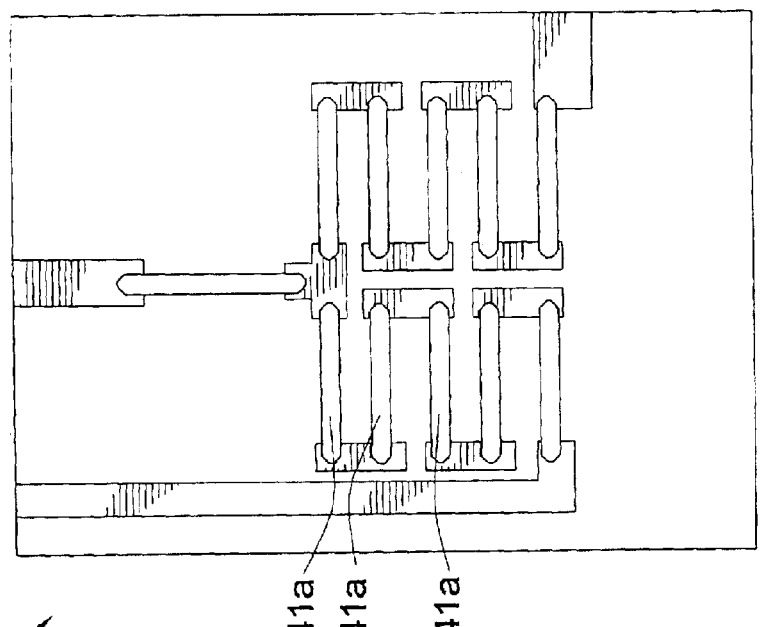
FIG. 3 is a view similar to FIG. 2 but with the induction coil removed.
Figure 2:
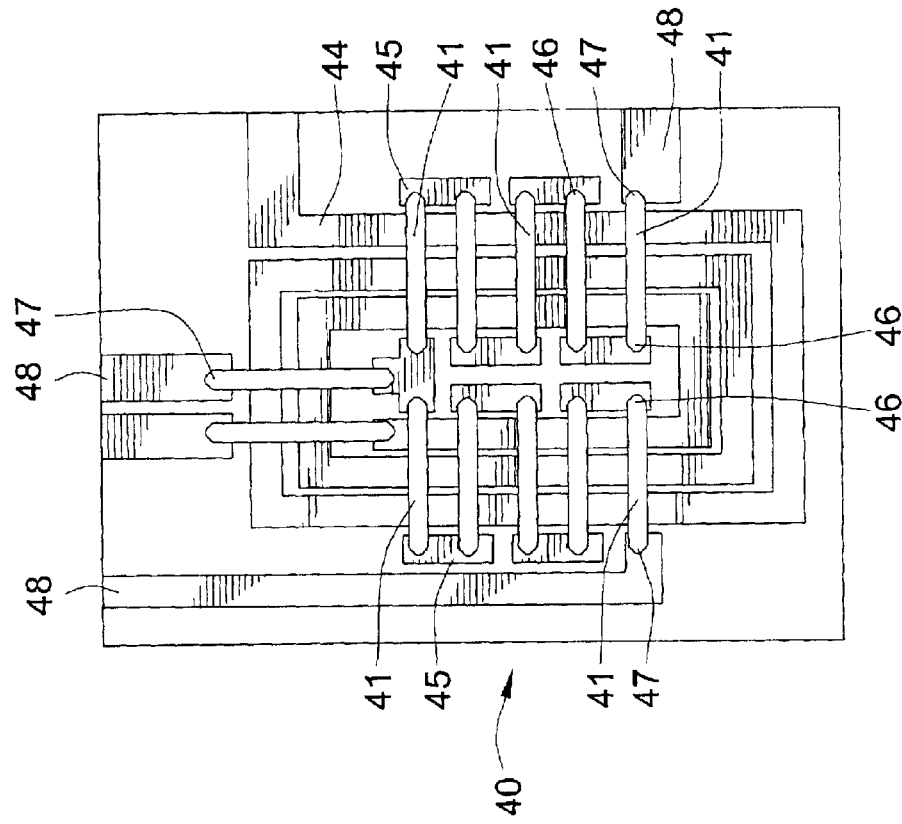
FIG. 2 is in an enlarged view of a multiple element GMR array of the type which can be used in a system according to the present invention.

Turning to FIG. 2, there is shown a small GMR array 40 of the type that can be used in the practice of the present invention. The array is a ten element array each element having a size of about 2×8 μm. Individual sensors are the long, rather thin, resistive elements identified by the reference numeral 41 and shown in 2 parallel columns of 5 sensors each. The 5 individual sensors in the parallel columns are wired in series, resulting in the GMR having two inputs and two outputs. It is recognized that the sensors in an array can be connected as individual sensors or in serial, parallel, and combinations of serial and parallel to create a larger sensor. The sensor 40 of FIG. 2 is of the type which has a magnetic coil 44 associated with the sensor elements 41 for controllably creating a field in the vicinity of the elements. The field is useful particularly when using paramagnetic particles that are magnetic only in the presence of an applied field. Such a field can be applied by a large coil associated with the entire array or by an integrated coil as shown in FIG. 2. In some applications of the present invention, the coil 44 is not required. In order to best illustrate that, FIG. 3 shows the GMR array of FIG. 2 but with the coil removed, such that the main portion of the structure illustrated in FIG. 3 is the sensors 41a which make up the GMR array 40a. As will be seen from FIGS. 2 and 3, the columns of sensors 41 are connected in series, and the 2 columns in parallel, by electronic traces such as 45 which interconnect pads 46 on the sensors and which further connect pads 47 which in turn are connected to output leads 48. It is connections to the leads 48 which are represented by the bus 36 connecting the GMR 21 to the interface 35 in the block diagram of FIG. 1.

In greater detail, GMRs, as currently available, consist of alternating ferromagnetic and conductive, nonmagnetic layers that form a 20–30 nm antiferromagnetic multilayer, and are typically capped with a 50–100 nm layer of passivating $Si_3N_4$ or other type of isolator. These devices exhibit a linear change in resistance with applied magnetic field. They are commercially employed in read heads on hard magnetic disks, and in that application can detect a bit as small as 50×10 nm on the surface of a disk. This spatial resolution is very compatible with the present invention.

Figure 4:
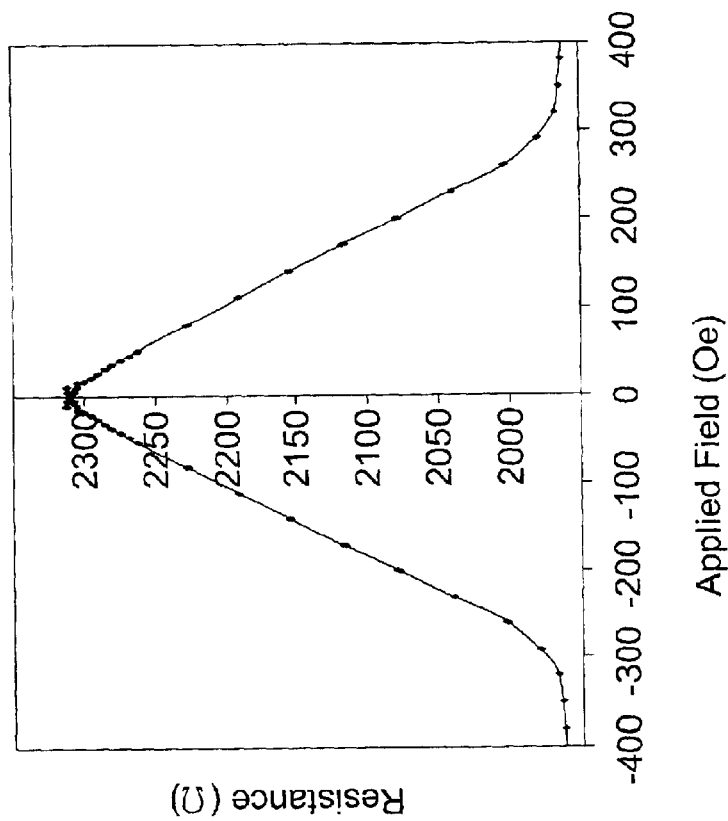
FIG. 4 is a diagram illustrating the response of the GMR to an applied magnetic field, and therefore illustrating the electrical output from a GMR resulting from changes in proximate magnetic field intensities.

The applicability of the GMR as a readout technology stems from its resistance being directly proportional to the magnitude of an applied magnetic field. FIG. 4 shows the typical behavior of a GMR by plotting the observed resistance for a 2×500 μm GMR as a function of applied field. As is evident, the resistance decreases linearly with applied field until the GMR approaches magnetic saturation. At saturation, there is no further change in resistance. The maximum decrease in resistance is typically 10–15% of the minimum resistance. GMR readout (i.e., production of the GMR output signal) is accomplished by passing a low current (e.g., 5 mA) through the device and measuring the voltage drop. Thus, the screening (e.g., modification or disturbance) of an external magnetic field that results from the presence of a magnetic label (e.g., magnetic particles) that is linked to a specific analyte represents the readout modality for microarrays.

It has been found that detection of magnetically-labeled reagents (e.g., superparamagnetic nanoparticles) using a GMR depends on several experimental parameters, including the number, size, and magnetic susceptibility of the particles; the separation between the particles and the GMR; and the size and background noise level of a GMR.

Assuming that $H_{app}$ (the applied magnetic field) is aligned with the most sensitive axis of the GMR, which usually lies along the plane of the multilayer stack, the following conclusions can be drawn. Directly under the particle, the resulting field from the magnetized particle ($H_{part}$) opposes $H_{app}$ and is written in MKS units as $H_{part} = -(4\pi/3)\chi_m (r^3/d^3) H_{app}$, where r and d represent the radius of the particle and separation between the particle center and GMR, respectively, and $\chi_m$ is the magnetic susceptibility. The total field ($H_{total}$) experienced by the GMR directly beneath the particle (i.e., $H_{total} = H_{app} + H_{pan}$) is then given by $$H_{total} = H_{app}[1 - (4\pi/3)\chi_m (r^3/d^3)]$$

This shows that the screening of $H_{app}$ by the particle, and therefore the magnitude of the resistance change, is dependent on the composition and size of the particle, and on the separation between the particle and the GMR.

Figure 5:
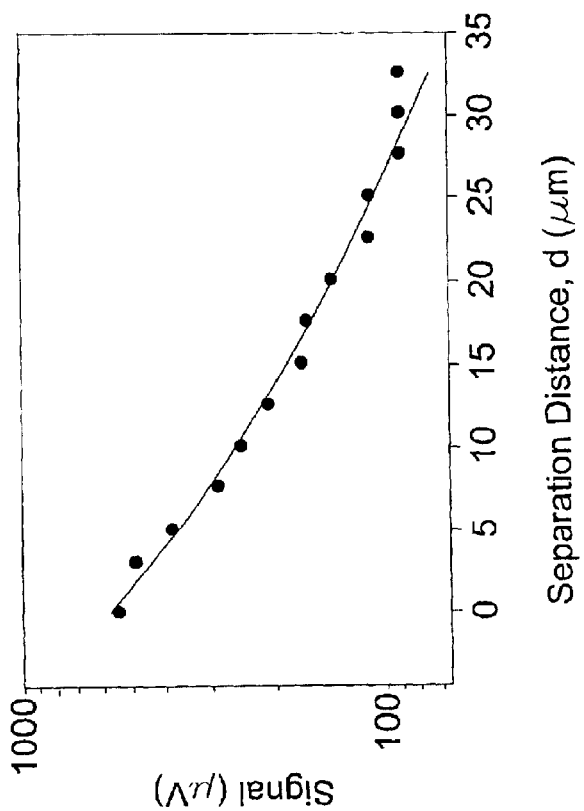
FIG. 5 is a plot illustrating the effect of separation between the GMR and the dispersion of magnetic microparticles on the GMR output.

In preliminary experiments designed to substantiate these factors, we attempted to verify the distance dependence expected for the resistance of the GMR as a function of the change and separation between a magnetic particle and the GMR. In this experiment, we glued a small dispersion of iron oxide particles ($\chi_m \sim 0.004$) to the end of an electrochemically-etched scanning tunneling microscopy (STM) tip and varied the tip-GMR separation with a micromanipulator. The results (solid circles) are shown in FIG. 5. We note that these data were obtained over a small portion of the negative slope of the plot shown in FIG. 4. FIG. 5 shows the effect of separation (d) between a GMR and dispersion of oxide microparticles on the GMR resistance. The experimental data have a noise level of about 0.5 μV, and the applied external field was 20 Oe. The solid line is a $1/d^3$ fit of the data following the dependence in the equation stated above.

This development supports the conclusion that the decrease in resistance as separation increases follows the general dependence predicted by the foregoing equation, i.e., a $1/d^3$ dependence. This confirms that practical bioanalytical assays can make use of and exploit this dependence.

With respect to the magnetic particles, several properties (e.g., the size and magnetic susceptibility) of the magnetic particles play a central role in controlling the magnitude of the GMR response. In general, particles with diameters less than 30 nm are preferred because many such particles are superparamagnetic, i.e., they are magnetized only when in a magnetic field. Particles are commercially available as suspensions of superparamagnetic magnetite that are coated with a coupling agent for receptor immobilization (70, 135, and 175 nm spheres) and suspensions with 3–20 nm particles of magnetite maghernitite, iron nitride ($Fe_xN$), Fe and Co. Particles that are permanently magnetic can also be used, such as ferromagnetic particles. However, while such particles can often be highly magnetic, the permanent magnetism tends to cause them agglomerate or cluster, which makes paramagnetic or superparamagnetic particles preferable. Thus to avoid clustering, paramagnetic or superparamagnetic particles are used, but an external field is required.

In summary, what has been disclosed is a chip-scale integrated GMR associated with microfluidic channels adapted to monitor various analytes (e.g., proteins, toxins, DNA, and water born microorganisms) without the need for surface-immobilization of capture molecules for binding recognition. The common problem of nonspecific binding is reduced, potentially decreasing the limit of detection. For detection, the invention utilizes the change in GMR response when the concentration of magnetic particles, and/or their distance from the GMR surface change.

The following will describe two techniques for detection. In the first, characterized as the direct mode, magnetically labeled analytes are monitored when flowing over a GMR. In the second (called the indirect mode) unlabeled analytes are counted by monitoring transient changes in the response of a GMR exposed to a background flow of magnetic particles. The transient changes are due to particle dilution and/or change in distance from the GMR surface, owing to a passing analyte molecule.

Figure 6:
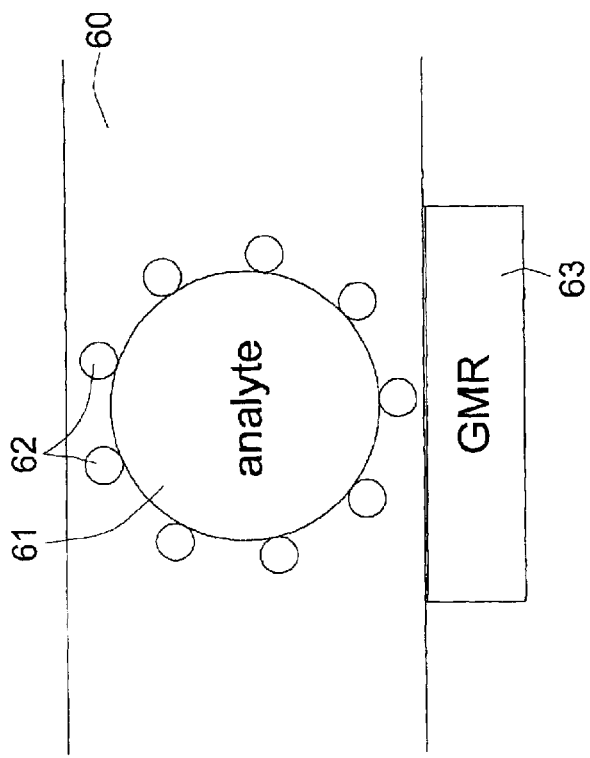
FIG. 6 is a diagram illustrating the direct detection mode.

Turning to FIG. 6, there is schematically illustrated the direct detection mode. A microfluidic channel 60 is shown in exaggerated scale. A single analyte particle 61 is shown within the channel, a plurality of magnetic particles 62 are adhered by binding agents to the analyte particle 61. A GMR cell 63 is illustrated at the base of the microfluidic channel 60. While FIG. 6 shows magnetic particles adhering to an analyte, it is recognized that the analyte itself could be inherently magnetic.

In the direct detection mode, superparamagnetic beads are coated with e.g., a biosensitive material to enable selective binding of a bacterium. The magnetically-labeled analytes are injected (following an off-chip filtration step to isolate the magnetically-labeled analytes) into fluidic channels positioned over GMRs, one of which is shown as GMR 63. Signal transients induced by the passage of these analytes over the GMR are recorded in real-time. It is also possible and often preferable to utilize on-chip pumping, sorting and direction. Such apparatus will be described below after completing the description of the indirect sensing mode. Using either on-chip or off-chip apparatus, the labeled analytes can be automatically manipulated, separated, and concentrated prior to their analysis by applying a magnetic field gradient, which directs/sorts, and consequently concentrates, the analytes. Such an integrated device can be used repeatedly following channel rinsing. Multi-analyte detection can be performed by using multiple channels and various labels that bind to specific analytes.

Figure 7:
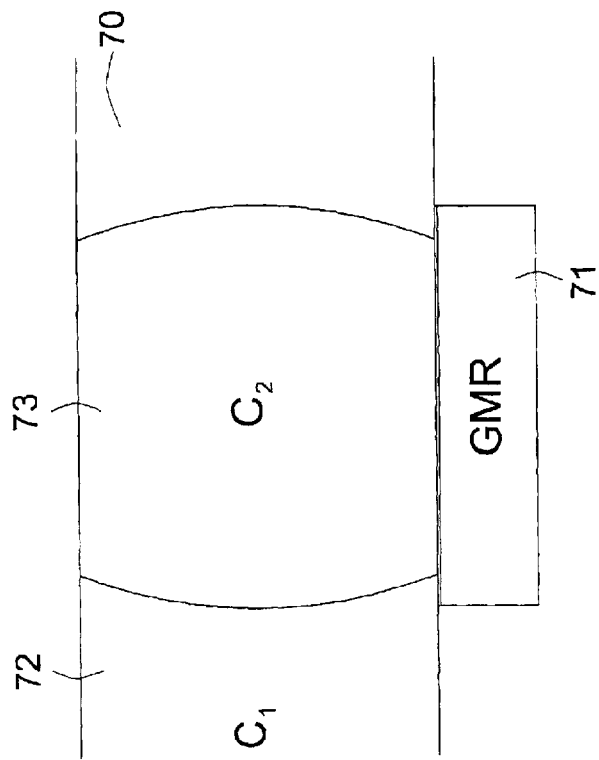
FIG. 7 is a diagram illustrating the indirect detection mode.

The indirect detection mode is illustrated in FIG. 7. There is shown another microfluidic channel 70 associated with a GMR element 71. $C_1$ represents the concentration of magnetic particles in the first fluid, in the present case taken as the carrier fluid 72. The bracketed section 73 contains fluid having a concentration of magnetic particles $C_2$, in the illustration intending to represent the analyte molecule. In normal practice, fluids of concentration $C_1$ continue to flow past the GMR 71 to provide a background signal representative of no analyte over the array. When analyte is present in the flow stream through the micro channel, concentration of the analyte at concentration $C_2$ will periodically pass the GMR and cause a transient response indicating the presence of the analyte fluid at the associated concentration level.

In the indirect detection mode, the resistance of a GMR exposed to a background stream of magnetic particles (e.g., diluted ferrofluids) is constantly monitored. Addition of a sample containing analyte molecules will affect the GMR reading. When an analyte molecule passes over the GMR a transient change in the GMR response is expected due to a local dilution and/or increased distance of the magnetic particles from the GMR surface. This detection mode is attractive because it does not require the use of specific labels, which further reduces effects of non-specific binding and eliminates the need for sorting and concentrating steps prior to detection. This approach is possible because of the high sensitivity of GMRs and the dependence of their response on the concentration and position of the magnetic particles. Because of this high sensitivity, this mode of detection can also be utilized to inspect the overall purity of liquids. To enhance detection, it is possible to manipulate the background concentration of the magnetic particles to a level adequate for monitoring transient changes in the resistance of the GMR due to the presence of non-magnetic analytes.

The indirect mode can be modified by coating the magnetic particles with e.g., biosensitive materials, to enhance the use of the dependence of the resistance on separation distance between the magnetic particle and the GMR. A target analyte molecule injected into a stream of surface-modified magnetic particles will interact with a magnetic particle, changing its distance from the GMR surface. This change in proximity will induce a change in the GMR resistance, which depends on the size of the analyte molecule. In addition to size, the binding specificity will also assist in analyte identification. This mode of detection can be used in conjunction with the other detection modes on the same chip.

As indicated above, small microfluidic channels on a chip can be used to carry and manipulate gasses, fluids, and particles in those gasses or fluids on the chip surface. These channels, when incorporated with integrated magnetic sensors and field generating straps, become versatile tools for doing magnetic sorting, magnetic pumping, and flow detection and measurement. The following disclosure will show how these three basic tools are made through electrical, magnetic, and mechanical design. First, the pumping and flowing will be described, and then detection.

In the figures referred to in the following descriptions that are cross-sectional views, the current direction is represented by the conventional symbols of "X" indicating current flowing into the page and "•" indicating current flowing out of the page. The size of the "X" or "•" indicates the magnitude of current relative to other magnitudes of current. Additionally, the field generated by the current is represented as a line encircling the current with the arrow indicating the direction of the field. The thickness of the arrow indicates the relative magnitude of the field with respect to other fields. In the figures that illustrate top views, the arrows located on metal straps indicate the direction of current flow and the thickness of the arrow indicates the relative magnitude of current with respect to other currents.

Force on a Magnetizable Object

The force that can be applied on a magnetized bead is proportional to the object's magnetization and the gradient in the field parallel to that magnetization. Ferromagnetic objects may have significant magnetization even in the absence of an applied field. In most of the objects we deal with in channels, however, (beads, paramagnetic particles, $O_2$ gas and other paramagnetic gases), the magnetization is linearly proportional to the applied field. For the purposes of this disclosure, we will assume paramagnetic types of materials with dimensionless magnetic susceptibility $\chi_m$ are being magnetized by a uniform external field H.

Using mks units:

$$B=\mu_0[H+M]$$

Units: (Webers/meter$^2$)=(Henries/meter)[(Amps/meter)+(Webers/meter$^2$)]

$$M=\chi_m \cdot H_{app}$$

$\chi_m$ is the dimensionless magnetic susceptibility

For convenience, we assume a spherical superparamagnetic or ferromagnetic particle along the lines of Dynal's M280 bead which has a diameter of 2.8 $\mu$m and a $\chi_m$ of about 0.05. The sizes and magnetic properties of all available magnetizable particles range over many orders of magnitude. A field along the x-axis will uniformly magnetize a bead to magnetization $M_x$, and induce a dipole moment p:

$$p=M(4\pi/3)a^3$$

where

α is the radius, M is the magnetization.

Units: (Webers/meter).

The force on the dipole p due to a magnetic field gradient is $$F=\nabla(H \cdot p)$$

Suppose the local magnetic field distribution in the region of the bead is such that $H_x \gg H_y$, $H_g$, and $\delta H/\delta_x \gg \delta H/\delta_y$, $\delta H/\delta_z$. Then the force on the bead is closely approximated by $$F_x=\delta H/\delta x \cdot p=(\delta H/\delta x)p=(\delta H/\delta x)((4\pi/3)Ma^3)=\chi_m \mu_o H_x(\delta H/\delta x)(4\pi/3)a^3$$

Easily achievable on-chip values for H and $\delta H/\delta x$ are 1000 A/m (12.5 Oe) and 2×10$^8$ A/m$^2$(2.5 Oe/$\mu$m), respectively. Also, a=10$^{-6}$ m, and $\chi_m$=0.05. So a typical force would be $$F=(0.05)(4\pi \times 10^{-7} \text{ Henries/m})(10^3 \text{ Amps/m})(2 \times 10^8 \text{ Amps/m}^2)(4\pi/3)(10^{-18}\text{m}^3)$$

$$F=52.6 \times 10^{-15} \text{ Newtons}$$

$$F=52.6 \text{ fN (femtoNewtons)}$$

For reference, assuming a bead has a mass density of 10 times water, a bead with a diameter of 1 $\mu$m will experience a gravitational force 51.3 fN. The values used for this calculation are fairly conservative. One could clearly increase the expected force on magnetizable particles by several orders of magnitude by increasing the external field, the gradient field, and the particles' susceptibility and volume.

Redirection and Sorting

One use for this kind of on-chip magnetic force is to redirect or sort magnetizable objects that are flowing in a channel. Applying a uniform field to magnetize the objects in a particular direction can be accomplished with an external coil. But the key point in this aspect of the development is that very large field gradients (>10$^8$ A/m$^2$) can be created on-chip due to the very small dimensions of the field generating current straps. The location and field from these straps can be controlled precisely, resulting in a known field gradient which is also limited in spatial extent. In contrast, an external magnet can create equally large gradients, but their magnitude and direction are not controllable on the scale of a few micron wide channel and they extend over very large regions of space. Thus, external magnets are difficult to use for multifunctional magnefluidic chips.

Figure 8:
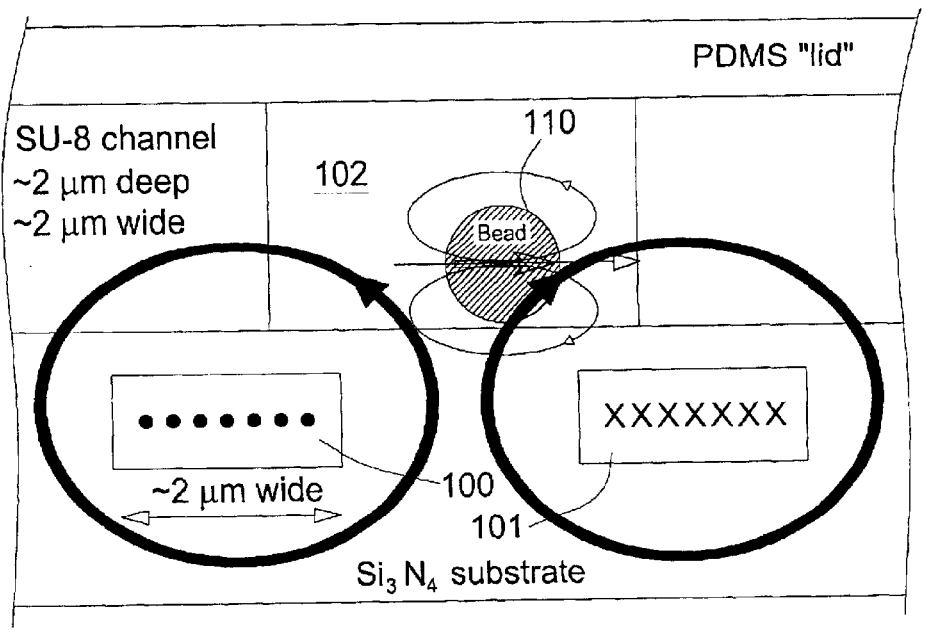
FIG. 8 is a cross-sectional view of a typical magnetic microfluidic sorter.
Figure 9:
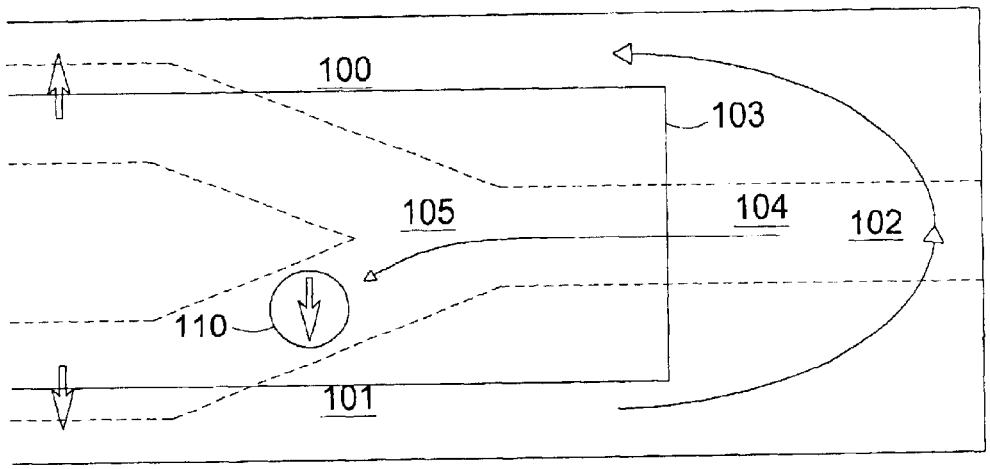
FIG. 9 is a top view of the sorter of FIG. 8 illustrating the currents, fields, and sorting action.

Schematic diagrams of a simple magnetic microfluidic flow sorter are shown in FIGS. 8 and 9. The basic concept is to have electrical current going in opposite directions in two adjacent buried metal straps 100, 101. The straps 100, 101 pass beneath the magnetic microfluidic channel 102 such that they run parallel to and on either side of the channel in a region 105 where the channel splits (FIG. 9). When a magnetized particle 110 passes over the sorter, it experiences a cross-channel force that is proportional to the current in the straps. This is because the field from these straps just above them has a large cross-channel gradient that is proportional to the strap current. The particle is attracted to and repelled by fields parallel and opposite to its magnetization, respectively.

FIG. 9 shows a top view of a magnetic microfluidic sorter. The fluid carrying magnetizable particles flows from right to left. In-plane magnetized (up or down) objects 110 in the fluid experience a force towards the leg of the current strap that generates a field parallel to the particle's magnetization. In FIG. 9, the force is down the page. If the current direction is changed in the strap, the force on the down-magnetized particle would be up the page. The dimensions in the figures are approximately representative. The channel could be 2 $\mu$m wide, and the two legs of the channel could be 2 $\mu$m apart. The strap tines would be 3 $\mu$m wide and separated by 3 $\mu$m. Again some adjustment of scale and relative sizes may be required to optimize the performance for a particular application. One important design aspect is that the portion of the strap that goes under the channel should be much wider than the "tines" of the sorter "fork" so that the field there is much smaller than in the sorter region.

In order for the sorter to truly work, the force on the particle must be large enough to push it to one side of the channel within the time the particle is in the sorter region 104, 105 (before the channel split). The chance of a given magnetized object being "sorted" can be increased by: 1) extending the sorting region up the channel (make the strap fork 103 start well before the channel split), 2) increasing the current through the strap, 3) decreasing the flow rate in the channel, and 4) increasing the magnetization of the object. Conversely, the chances of an object being sorted can be decreased by doing the opposite things (shorter sorting region, lower current, higher flow rate, decreased magnetization). Because the last factor, the magnetization of the object, is due in part to the magnetic properties of the particle, it is possible to sort out particles of differing magnetic properties. One could vary the magnetization of the particles by changing the susceptibility, the fractional composition of magnetic material (many magnetizable particles are a core of magnetic material surrounded by a non magnetic coating, or a matrix of magnetic and non magnetic material). Additionally, the force required for a successful "sorting event" will be proportional to the particles cross sectional area, because the force must move the particle through the fluid. So the magnetization per unit cross-sectional area will also determine whether a particle is sorted or not. Additionally, one could sort particles by their saturation magnetization by applying a magnetic field and monitoring when the magnetization does not increase. Thus, there are several ways to create sorters which not only separate magnetic from non magnetic objects, but also sort varying magnetic objects by their specific properties.

Smallest Beaker

The variable magnetic material sorting feature has many uses. Clearly, it can be used to create a sample of monodisperse magnetized objects. If certain chemical or biological species are attached to the magnetizable particles, the sorter can be used to move these species in a controlled way. In fact, a magnetic particle with a known species attached to it can be thought of as the world's smallest beaker. Because small particles can be coated with "functionalizing groups" which determine what species will stick to it, one can prepare a volume of a desired species consisting of only the surface area of one magnetic particle. Then with the sorting apparatus, this nano-beaker can be manipulated in the channels and directed to a desired reaction chamber.

Pumping

The same forces used to sort magnetizable objects can also be used in a pumping mechanism. This is accomplished by having 3 separate straps under the channel with their oscillating currents out of phase by 60 degrees. The situation is similar to the simple sorter in that a gradient field must be created to exert a force. In the pumping case, though, the gradient must also vary in time to cause the particles to move through the channel. When the external magnetizing field is along the channel (e.g., $\hat{x}$), the moving force along the channel is proportional to the local field gradient with respect to the channel $dH_x$ dx. One could also use a perpendicular (e.g., $\hat{z}$), magnetizing field in which case the moving force would be proportional to $dH_z dx$.

Figure 10:
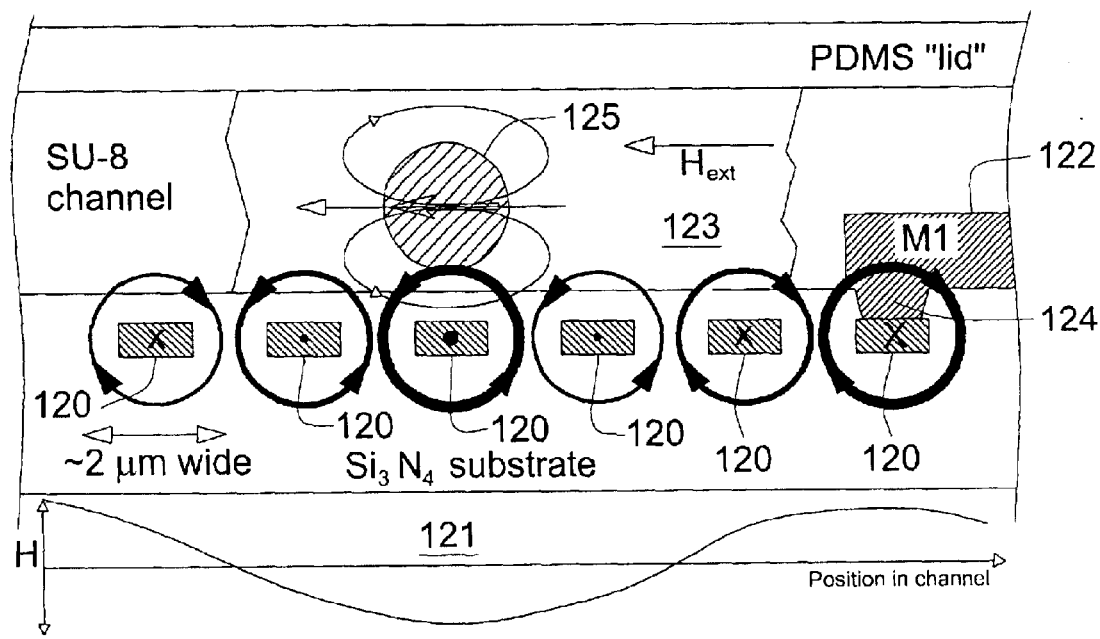
FIG. 10 illustrates in cross-section the architecture of a microfluidic pump.

Turning to FIG. 10, Metal 0 straps 120 beneath the channel (flowing left to right) create a sinusoidally oscillating (with respect to position) distribution of field parallel to $H_{external}$ (see 121) along the channel 123. Metal 1 shown at 122 is used to connect the straps in such a way to make this into three separate interwoven electrical current paths. The Metal 1 interconnect is only shown in one place here so that it does not obstruct the view of the channel. Also shown only once is the vertical via 124 from Metal 1 to Metal 0. The approximate field magnitude along the channel is indicated by the H plot beneath the cross section (positive field is taken to be from left to right. Magnetizable objects such as particle 125 are drawn to the largest field parallel to their magnetization, which in this case is at the lowest point in the plot.

Figure 11:
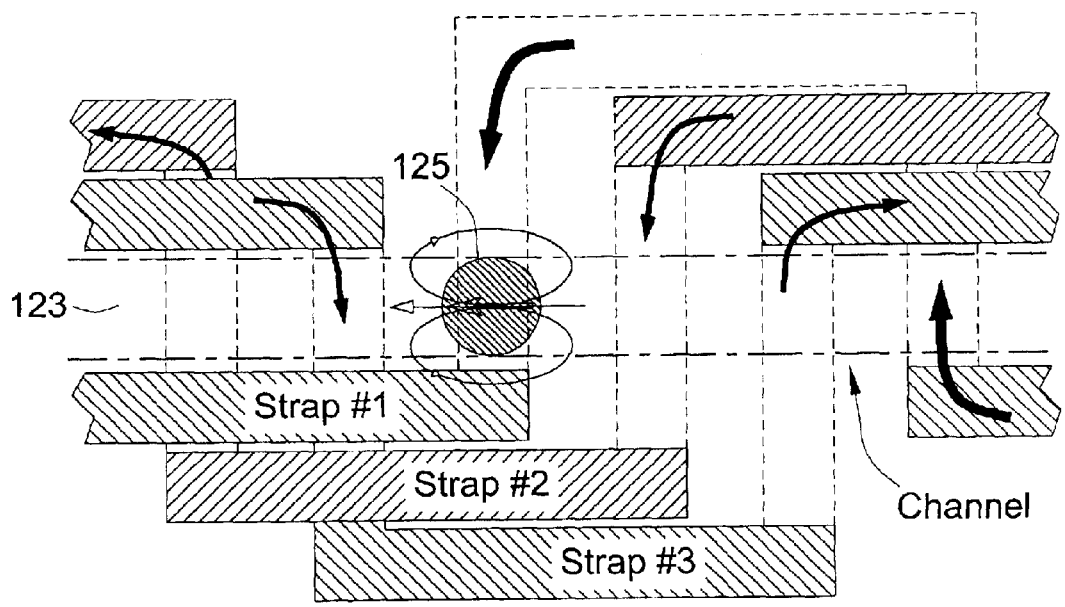
FIG. 11 shows the top view of the pump of FIG. 10 and better illustrates the phase relationship between the electrical current in the under-channel conductors.

FIG. 11 shows a top view of the pump. There are three separate current straps 1, 2, 3 as labeled. The non-shaded regions are the lowest metal layer (Metal 0) while the shaded regions are up one layer (Metal 1). Not indicated are the vertical vias between Metal 0 and Metal 1. The dashed line represents the channel formed above the GMR elements. The magnetized objects are attracted to the region where the field is largest and parallel to their magnetization. They are repelled from the regions of largest antiparallel fields. What is drawn is a static situation. In order to pump, the electrical current in the three channels must oscillate in time and be appropriately phased.

In order to achieve the field distribution shown at the bottom of FIG. 10, the electrical current in straps 1, 2, and 3 should be C, C/2, and −C/2 respectively. The time dependence of these currents is $I_1 = C \cos(2\pi\omega t)$, $I_2 = C \cos(2\pi\omega t + \pi/3)$, $I_3 = C \cos(2\pi\omega t + 2\pi/3)$ where $2\pi\omega$ is the frequency, f, of oscillation in Hz. Because each successive crossing of a strap beneath the channel carries the current in the opposite direction from the previous crossing, the field from current in that strap is $\pi$ out of phase from that from the previous crossing. In this way, there are six distinct field phases generated in the channel by the three distinct straps. Each phase is separated by $2\pi/6$.

As the gradient moves in time, the magnetizable objects will experience a force along the channel. The region of largest force will be that of highest gradient (at $\pi/2$). If this force is significantly larger than the opposing forces from fluid in the channel, magnetized particles will be pushed along the channel at a rate of 6 fd, where d is the separation from one strap crossing to the next. If the force is not large enough, magnetized objects will not move fast enough to keep up with the moving gradient, and hence have a lower pumping efficiency.

Induced Flow Rate

Poiseuille's Law says that $$I_v = vA = \pi r^4 \Delta P / 8 \eta L$$

Physics, Tipler p. 390, $2^{nd}$ ed. 1982

(velocity)(cross-sectional area)=$\pi$(tube radius)$^4$ (pressure change)/ 8(viscosity)(Length)

This can be adjusted for rectangular flow channels to be $$I_v = [\Delta P/L][w^3 h^3 / 16\eta(w+h)^2]$$

Design and Fab. of Fluidic Systems, Verpoorte and Harrison, Lecture #8 LabAutomation 2000, Jan. 22, 2000

The main point is that the flow rate is proportional to the pressure drop per unit length in the channel. Even though the absolute pressure exerted by the pump is very small, the drop per unit length is much higher because of the tiny dimension of the pump. Suppose the force on a 1 $\mu$m×1 $\mu$m magnetizable particle is $1.2 \times 10^{-12}$ N, and the force per unit area is 1.2 N/m$^2$=1.2 Pa. If the distance from one gradient maximum to the next is 12 $\mu$m, then $\Delta P/L = 1 \times 10^5$ Pa/m. Using 2 $\mu$m for the channel width and height, and $1 \times 10^{-3}$ s.Pa (second-Pascal) for the viscosity, then the volume flow rate is $$I_v = [1 \times 10^5 \text{ Pa/m}][64 \times 10^{-36} \text{ m}^6]/[16(1 \times 10^{-3} \text{ s.Pa})(16 \times 10^{-12} \text{ m}^2)] = 2.5 \times 10^{-17} \text{ m}^3/\text{s} = 2.5 \times 10^{-14} \text{ liter/s}$$

The cross sectional area is $4 \times 10^{-12}$ m$^2$, so the velocity is $6.25 \times 10^{-6}$ m/s, or 6.25 $\mu$m/s. This could be a very convenient flow rate for the small dimensions under consideration.

Velocity Measurement

Figure 12:
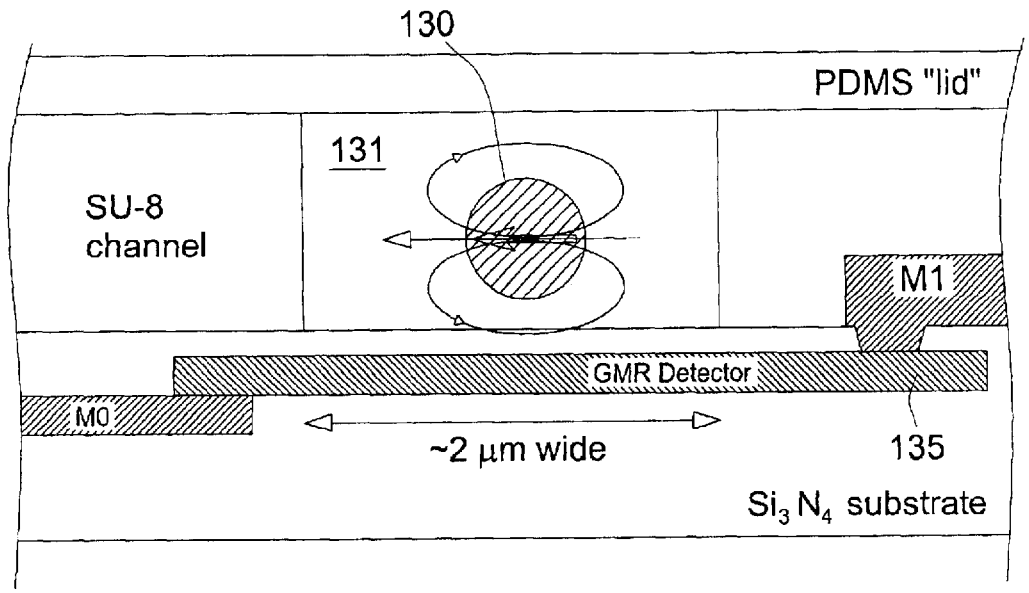
FIG. 12 is a cross-sectional view illustrating a microfluidic channel associated with a GMR detector arranged as a velocity detector.
Figure 13:
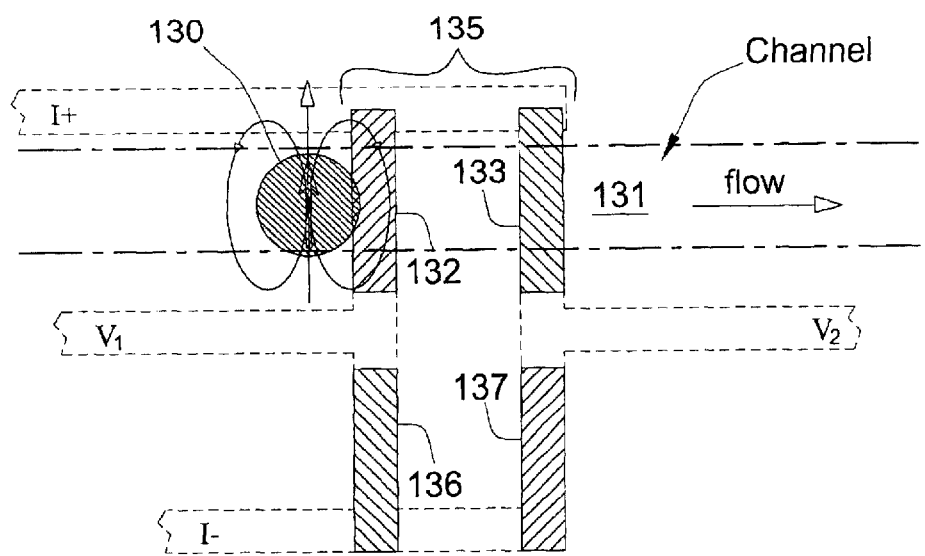
FIG. 13 is a top view of the velocity detector of FIG. 12 better showing the positioning of the sense resistors and reference resistors making up the GMR detector.

As illustrated in FIGS. 12 and 13, the velocity of discrete magnetized objects 130 can be measured in a channel 131 using a pair of magnetoresistive detectors 132, 133. These are thin film metal resistors whose resistance changes in proportion to the magnetic field incident upon them. FIGS. 12 and 13 indicate one possible configuration using GMR (Giant Magnetoresistive) detectors 135 to measure the velocity of a flowing magnetized particle 130. In these drawings, the particle is magnetized in the plane of the sensor along its sensitive axis. The GMR detector elements 132, 133 are spaced apart by some known distance, preferably on the order of the particles diameter. As the particle passes over each of the two GMR detectors, it momentarily changes the resistance of that resistor without changing that of the other detector or the reference resistors 136, 137. Hence, a change in voltage is measured between $V_1$ and $V_2$. There are momentary voltage changes while the particle is over each of the two sense resistors. The velocity of the particle is calculated simply by dividing the distance separating the two detectors by the time separation between the two momentary voltage changes.

The size of the resistance change will be dependent upon the size of the magnetizing field, the separation from the particle to the detector, the magnetic properties of the particle, and the size of the particle. Assuming the same particle as was described above, the two components of the dipole field at distance r from the center of a bead are $$H_r = \chi_m H_{app}(8\pi/3)(\alpha^3/r^3) \cos(\theta) \text{ and } H\theta = \chi_m H_{app}(4\pi/3)(\alpha^3/r^3) \sin(\theta)$$

where $\theta$ is the angle between r and M (M is parallel to $H_{app}$).

Figure 14:
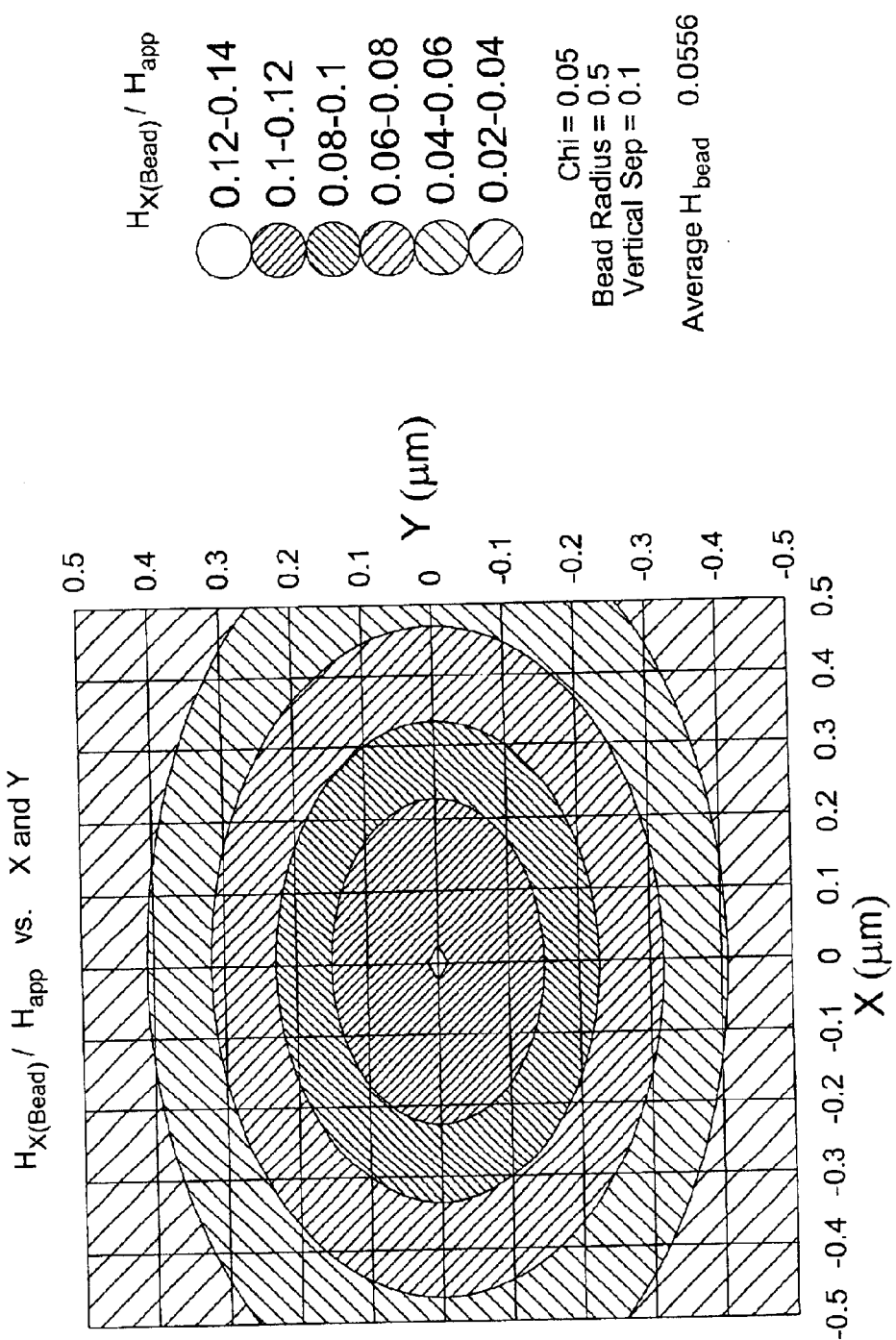
FIG. 14 is a plot useful in understanding the sensitivity of the velocity detector of FIGS. 12 and 13.

The direction of $H_{bead}$ from a bead in a uniform applied field in the plane of the page from right to left is roughly depicted in FIG. 12. Note that the field directly under the bead 130 (at $\theta = \pi/2$) due to its magnetization directly opposes the applied field. Setting $\chi_m = 0.05$, a=0.5 $\mu$m, and v=0.1 $\mu$m, the X-component of $H_{bead}$ can be calculated as a function of X and Y. The results of this calculation are shown in FIG. 14. Note that the fields plotted in FIG. 14 are in the opposite direction from the applied field. The total field on the GMR detector is the sum of $H_{app}$ and $H_{bead}$. Since $H_{bead}$ is always opposite to but smaller than $H_{app}$, the net field will never be greater than $H_{app}$, or less than zero. The average effect in the given example is $H_{bead} = 0.05 H_{app}$, so the net field is $H_{total} = 0.95 H_{app}$. Consequently, the detector must be sensitive to changes of about 5% in the local field. This is not particularly difficult.

This velocity measurement could potentially be used in applications like electrophoresis, chromatography, and other things where the flow of various species in a channel are compared.

It is often desirable to mix together two different fluids flowing in the same channel. This can sometimes be difficult due to the laminar type flow that is present in typical microfluidic system where the Reynolds number is well under that required for turbulent flow. The same structures used to sort and pump could be used to induce mixing. A simple example would be to use the sorter type fork under a single (not splitting) channel, and oscillate the current in the fork so that any magnetizable particles in the channel are forced from side to side at the frequency of oscillation. If mixing is the primary objective, particles with much higher magnetism could be used than the typical 0.05 susceptibility.

A example of how the present invention can be used as a mixer and detector is to use the sorter type with a single channel as a magnetic flow cytometer to label, sort, and detect an analtye. In this example, E Coli O157:H7 shall be used as the analyte. Other types of analytes can be used. The E Coli O157:H7 sample to be screened is introduced to the GMR chip and mixed with magnetically labeled anti E Coli by alternating the current flowing through the current strap and allowed to incubate to ensure efficient label coverage of any E Coil O 157:H7 present. The labeled analyte and excess label are then flowed across the sorting element (i.e., the current strap). As the density of magnetic labels on the analyte is greater than the density of unbound labels in solution, the analyte can be separated from the "magnetic solution" in the magnetic gradient created by the current straps. The labeled E Coli O157:H7 is flowed across the GMR sensing elements affecting an electrical response indicative of the concentration of analyte. Alternatively, detection can be made by sensing changes in the background signal as the analyte passes the sensing element.

Other Materials

It should be noted that the forgoing discussion on magnetizable objects can be extended to many types of materials beyond typical paramagnets, including ferromagnets and diamagnets. Some interesting material possibilities include alloys of Ni, Fe, and Co, for ferromagnetics; Gd, Dy, Tb and compounds of these for high paramagnetic response; and Bi, and $Al_2(SO_4)_3$ for relatively high diamagnetic response.

SUMMARY

In summary, what has been described is a new apparatus and method that utilizes a GMR for on-chip manipulation and detection of analyte concentration or distance. The detection system does not require binding reception at the surface of the GMR, and has operating modes that are suitable for detection of low levels of various chemicals and bioanalytes. Detection is based on analyte concentration, size, label and binding properties. Detection can be extended to measuring particle velocity in microfluidic channels.

As a further advantage integrated GMRs/microfluidic channels can be used repeatedly by rinsing the channels between measurements. Multi-analyte analysis is possible through the design of multiple channels and associated GMRs on a chip-scale device. Several detection modes can be used on the same chip-scale device. For example, both the direct and indirect detection modes can be operated on the same chip-scale device without interference between them.

Application of the techniques is simple and does not require immobilization of captured molecules on the GMR surface. In the indirect mode the need for surface immobilization and other specific binding chemistries is eliminated. As such, non-specific binding effects are reduced, potentially decreasing the limit of detection.

With respect to the indirect mode, it can be used to inspect the overall purity of liquids. In the indirect mode, analytes can also be identified by chemically modifying the surface of the magnetic particles flowing over a GMR to enable binding of target analytes. Such a binding effect will result in a change in the GMR response that depends on the analyte size. This mode can enhance detection sensitivity and enable analyte identification based on size and/or specific binding.

The foregoing description of various preferred embodiments of the invention has been presented for purposes of illustration and description. It is not intended to be exhaustive or to limit the invention to the precise forms disclosed. Obvious modifications or variations are possible in light of the above teachings. For example, the measuring, sorting, and pumping methods can be applied to particles in a vacuum and the measuring methods can further be used to statically measure fluids and gasses. Additionally, structures similar to GMRs can be used such as Hall Effect devices, anisotropic magnetic resistance (AMR) and spin dependent tunneling (SDT). The embodiments discussed were chosen and described to provide the best illustration of the principles of the invention and its practical application to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally, and equitably entitled. To the extent required for clarity or completeness, the disclosures of all publication patents and publications cited herein are incorporated by reference.

What is claimed is:

1. A method of monitoring analyte flowing in fluid streams comprising the steps of:

providing a giant magnetoresistive sensor having at least one sensing element which produces electrical output signals that vary dependent on changes in the magnetic field proximate the sensing element;

providing a stream including the analyte, the stream having a magnetic property dependent on the concentration and distribution of analyte therein;

flowing the stream past the giant magnetoresistive sensor in sufficiently close proximity to cause the magnetic properties of the stream to produce electrical output signals from the giant magnetoresistive sensor; and monitoring the electrical signals produced by the giant magnetoresistive sensor as an indicator of at least one of an analyte concentration, an analyte distribution, and an analyte magnetic property in the stream flowing past the giant magnetoresistive sensor.

2. The method of claim 1 in which the step of providing a stream including the analyte comprises magnetically labeling the analyte for direct detection thereof.

3. The method of claim 2 wherein the step of providing a stream including the analyte comprises injecting the analyte into the stream.

4. The method as set forth in claim 1 wherein the step of providing a stream including the analyte comprises providing a background stream of magnetic particles flowing past the giant magnetoresistive sensor and adding unlabeled analyte to the stream whereby the GMR output represents an indirect measure of the presence of the analyte.

5. A detecting system for monitoring the concentration of analyte present in a flowing fluid stream, the detecting system comprising in combination:

a giant magnetoresistive sensor having at least one sensing element for detecting localized changes in the magnetic field proximate the sensing element;

microfluidic channels associated with the giant magnetoresistive sensor for providing microfluidic channels closely proximate the sensor element, the proximity being such that magnetic particles flowing in the channels will cause an output from the giant magnetoresistive sensor indicative of at least one of the concentration, distribution, and magnetic properties of magnetic particles;

a source of analyte in a fluid stream altered such that the fluid stream has a magnetic property related to the concentration or distribution of analyte in the stream, the source being connected to the microfluidic channels for flowing a stream including the analyte past the giant magnetoresistive sensor; and an electrical monitor responsive to the giant magnetoresistive sensor for measuring and recording changes in the output signal as an indication of the magnetic properties and therefore analyte concentration or distribution in the stream flowing past the giant magnetoresistive sensor.

6. The detecting system of claim 5 further comprising a magnetic field generator for controllably creating a magnetic field proximate to the at least one sensing element.

7. The detecting system of claim 5 wherein the giant magnetoresistive sensor comprises an array of sensing elements arranged in series.

8. The detecting system of claim 5 wherein the giant magnetoresistive sensor comprises an array of sensing elements arranged in parallel.

* * * * *

UNITED STATES PATENT AND TRADEMARK OFFICE
CERTIFICATE OF CORRECTION

PATENT NO. : 6,736,978 B1 Page 1 of 1
APPLICATION NO. : 10/017467
DATED : May 18, 2004
INVENTOR(S) : Marc D. Porter et al.

It is certified that error appears in the above-identified patent and that said Letters Patent is hereby corrected as shown below:

Title Page item 73

Assignee, add -- NVE Corporation, Eden Prairie, Minnesota --.

Signed and Sealed this

Fifth Day of February, 2008

JON W. DUDAS
*Director of the United States Patent and Trademark Office*